United States Patent [19]

Walker

[11] Patent Number: 4,962,384
[45] Date of Patent: Oct. 9, 1990

[54] MICROWAVE ANTENNA APPARATUS

[76] Inventor: Charles W. E. Walker, 591 West 57th Avenue #301, Vancouver, B.C., Canada

[21] Appl. No.: 443,054

[22] Filed: Nov. 28, 1989

Related U.S. Application Data

[60] Continuation of Ser. No. 129,609, Dec. 7, 1987, abandoned, which is a division of Ser. No. 836,964, Mar. 6, 1986, Pat. No. 4,727,311.

[51] Int. Cl.$^5$ ............................................ H01Q 13/00
[52] U.S. Cl. .................................... 343/786; 343/703; 324/640
[58] Field of Search ........................ 343/786, 703, 722; 324/637, 639, 640, 643

[56] References Cited

U.S. PATENT DOCUMENTS

| | | | |
|---|---|---|---|
| 2,398,096 | 4/1946 | Katzin | 343/786 |
| 2,825,060 | 2/1958 | Ruze | 343/786 |
| 3,100,894 | 8/1963 | Giller et al. | 343/786 |
| 3,205,499 | 9/1965 | Raburn | 343/786 |
| 3,305,870 | 2/1967 | Webb | 343/786 |
| 3,369,197 | 2/1968 | Giger et al. | 343/786 |
| 3,555,553 | 1/1971 | Boyns | 343/786 |
| 3,818,333 | 6/1974 | Walker | 343/785 |
| 4,258,366 | 3/1981 | Green | 343/786 |
| 4,368,421 | 1/1983 | Glander et al. | 324/640 |
| 4,727,311 | 2/1988 | Walker | 324/58.5 X |
| 4,788,853 | 12/1988 | Bell | 324/640 |

FOREIGN PATENT DOCUMENTS 1210696 10/1970 United Kingdom ............... 343/786

*Primary Examiner*—Rolf Hille
*Assistant Examiner*—Le Hoanganh
*Attorney, Agent, or Firm*—Klarquist, Sparkman, Campbell, Leigh & Whinston

[57] ABSTRACT

A microwave measurement apparatus is disclosed for measuring an unknown property of a test material, such as moisture content, by transmitting microwave beams through such material so that a portion of the beam energy is absorbed by the moisture or other property. Two microwave input signals of different frequencies are used to form the microwave beams and the corresponding attenuated received signals are compared in order to compensate for the presence of a component in the test material, such as foundry molding sand, which is not being measured but which also absorbs microwave beam energy. To determine the density of the test material in the event of changes in such density, one of the microwave signals is used to measure the phase shift of the corresponding received signal and produce a phase shift output signal. A single microwave antenna having two microwave signal connection is employed to transmit the two microwave beams of differnet frequency without interference and another antenna of the same type receives such two beams to produce the two attenuated received signals. The two attenuated received signals of different frequency and the phase shift output signal are combined in a signal processor to produce a percent moisture content signal.

6 Claims, 3 Drawing Sheets

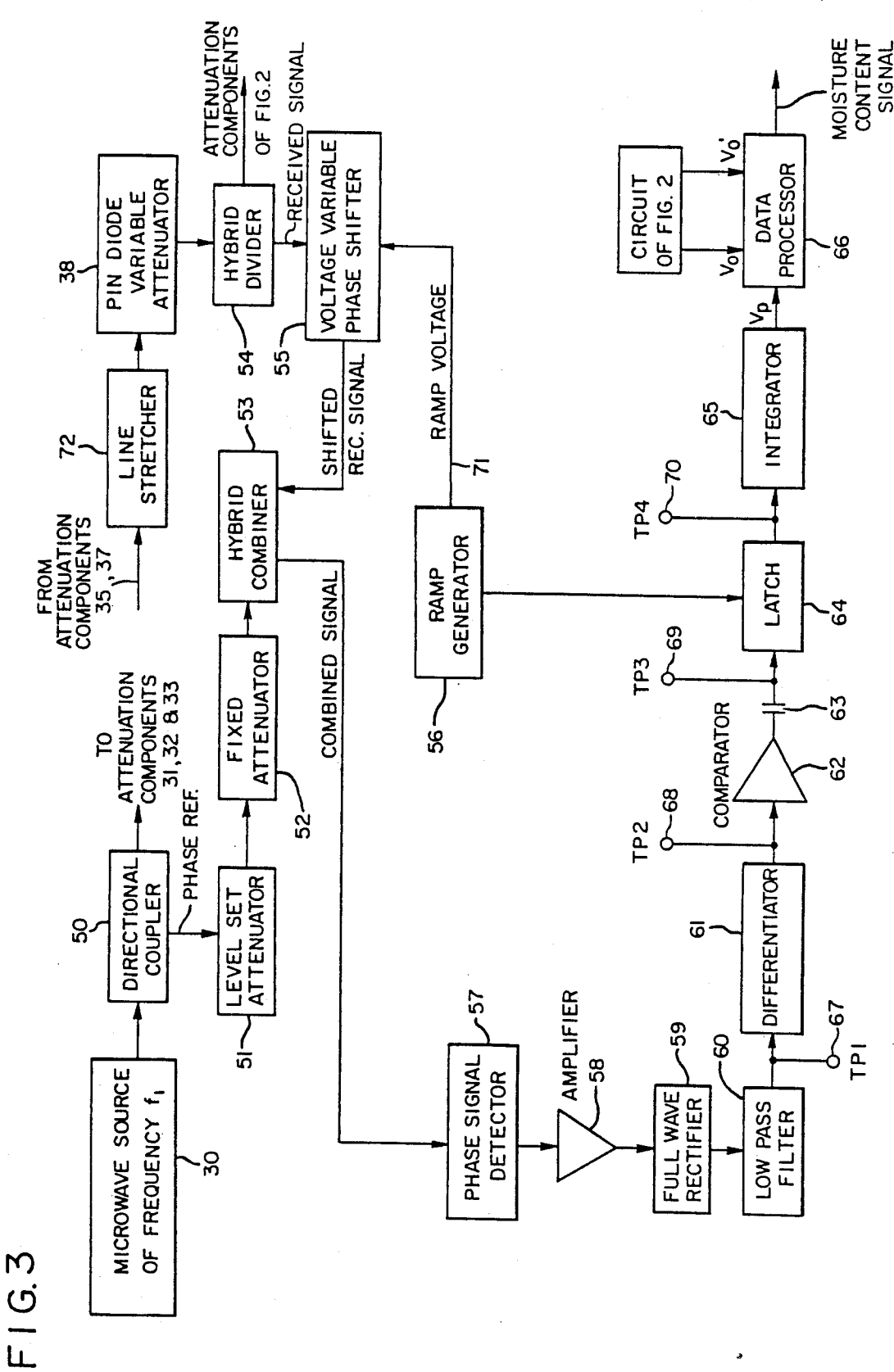

MICROWAVE ANTENNA APPARATUS

This application is a continuation of application Ser. No. 07/129,609 filed Dec. 7, 1987 now abandoned. which is a division of application Ser. No. 836,964, filed Mar. 6, 1986 now U.S. Pat. No. 4,727,311.

BACKGROUND OF THE INVENTION

The present invention relates to the measurement of unknown properties of materials, such as moisture content or dielectric constant, using microwaves and in particular to the measurement of the moisture content of a material by transmitting microwave beams through such material so that a portion of the beam energy is absorbed by the moisture or other property. This percent moisture measurement is achieved with good accuracy in spite of the presence in the test material of another microwave absorbing property or component in variable amounts, by measuring attenuation using two microwave signals of different frequency and determination of the density of the test material by measuring the phase shift of the received signal produced by one of such signals when its corresponding microwave beam is transmitted through the test material. The invention also includes a microwave antenna with two microwave signal connections for the two different frequency signals properly positioned in order to efficiently transmit or receive two microwave beams of different frequency with the same antenna without interference.

The present invention is especially useful in measuring the moisture content of foundry molding sand and coal. In the previous U.S. Pat. Nos. 3,696,079, 3,818,333 and 4,475,080 of Charles W. E. Walker issued Sept. 19, 1972, Jun. 18, 1974 and Oct. 2, 1984, respectively, and in the paper "Instrumentation for the On Stream Analysis of Ash Content and Moisture Content in Coal Cleaning Plants" by Gunter Fauth, et al, published at the annual meeting of S.M.E. and A.I.M.E. at Los Angeles, Calif. Feb. 26 to Mar. 1, 1984, microwave moisture measurement apparatus is disclosed. However, these prior apparatus do not employ two microwave beams of different frequency to determine the amount of moisture attenuation of the microwave beams by the test material, and do not measure the phase shift of one of the two attenuated received microwave signals to determine test material density for measurement of the percent of moisture content, in the manner of the present invention. In addition, they do not show a microwave antenna which is capable of transmitting or receiving two microwave beams of different frequency at the same time without interference in the manner of the invention.

The invention is directed to the accurate measurement of the moisture content of a wide range of solid and liquid materials. In the above noted patents, it is shown that the absorption of microwave energy from a microwave beam transmitted through the material is capable of providing accurate information on its moisture content. The present inventor has found, however, that in all materials there are interfering effects or other factors present in the material, in addition to the amount of water present, which affect the microwave absorption.

All substances in the dry state produce some microwave absorption. In some, this microwave absorption is constant but in many of the materials which are industrially important, it is not constant and must be measured by an independent means if accurate measurement of moisture is to be obtained. In some cases, for example, the dry attenuation of the microwave is due to the dry substance being electrically conductive. If this is true in the macroscopic sense, the substance is probably not amenable to measurement by microwaves but many substances such as foundry . molding sand and most coals are not electrically conducting in the macroscopic sense, yet contain microscopic particles or aggregates of atoms which are conductive and which, as a result, attenuate a microwave signal passed through the substance. In the case of both coal and foundry sand, this observed dry attenuation is thought to be due to elemental carbon particles, possibly in the form of small graphite crystalites. Finely divided metallic particles could have the same effect. Whatever the cause, the microwave attenuation due to such electrical conductivity is not frequency dependent, and so is markedly different from the water resonant absorption. The same is true of ionic conductivity which is another form of electrical conductivity and may arise from the presence of salts or of acids or bases in the substance being measured since any of these will dissolve in any water which is present to produce ions. Ionic conductivity will not contribute to dry attenuation but will affect the microwave attenuation so as to add to the moisture sensitivity in proportion to the ionic concentration. If this electrical conductivity of the dry material is not constant or the ionic concentration varies, then an independent measurement is needed to account for it if accurate moisture measurement is to be obtained.

In the microwave method of moisture measurement, the microwaves are passed through the test material and therefore sense a certain volume of material and are absorbed in proportion to the number of water molecules in that sense volume. The measurement signal is therefore proportional to the mass of water per unit volume in the material. To express this as percent water requires that the mass of material in the volume sensed be known. This may require a measurement of both the thickness of material through which the microwaves are passed and the density of the material in that volume.

Yet another factor which affects the microwave moisture measurement readings is that some of the water present becomes bonded to the material. This bonding may be chemical, such as hydrogen bonds or may be physical, as for example Van der Waals forces. In either case, the water molecules so bonded are not free to rotate as free molecules and so do not exhibit the resonant interaction with microwaves. Except for hydrogen bonding of water to cellulose and starch molecules which produce a square law relationship between microwave attenuation and percent water, I have found that almost all substances exhibit an interaction which appears to be a surface bonding phenomenon because it is dependent on particle size and particularly on the finest particles present. Thus, in pure silica sand there is effectively no bonding to a coarse grade but over 1 percent water bonds to 32 mesh grade sand. The net effect of the bonding in most substances, other than the organic ones mentioned above, is to halve the microwave attenuation up to the saturation level at which all the available bonds are satisfied. Beyond this point the attenuation becomes normal. For accurate moisture measurement through this saturation level, it is necessary that this level be known and that it be measured if it is not constant. This generally requires a knowledge of the fines content. Thus, in foundry molding sand it is the finely powdered Bentonite clay which establishes this level.

To eliminate these disturbing factors and for accurate moisture measurement, it is essential therefore that at least three independent measurements be made. Only in special cases, can some of these be replaced with constant subtractors or divisors or by periodic manual adjustments as, for example when lower accuracy is acceptable, or when measuring some substances such as ammonium phosphate fertilizer in which the ionic conductivity is directly proportional to the amount of water present and so may be accounted for by a constant calibrating factor. In some other cases where moisture determination is only required over a limited range of moisture which is known to be either wholly below or wholly above the level at which bonding is saturated, it may not be necessary to measure this level.

It is therefore the specific purpose of this invention to provide the additional independent measurement means, in addition to the simple microwave attenuation, which are needed as stated above to provide accurate moisture measurement.

The present inventor has determined that the effect of dry attenuation can be eliminated by making microwave attenuation measurements at two different microwave frequencies. Because this dry attenuation is not frequency sensitive, the difference between the attenuation signals at the two different microwave frequencies is independent of the dry attenuation and depends only on the water present. This dual frequency measurement also eliminates the effect of variations in ionic conductivity when this is a concern. It is perhaps worth noting that there are some special cases such as alcohol and heavy water in which dry attenuation is frequency sensitive because these substances have their own resonant interaction with microwaves within the frequency range used for moisture measurement; clearly however, for this reason, microwaves cannot in any case be used to measure moisture in such substances unless another water resonance is available which is free of this restriction.

The present inventor has also determined that the density of the material in the microwave path can be measured using the same microwave beam as is used for one of the attenuation measurements by determining the change of phase of the microwave signal as it passes through the material. Like the attenuation, the phase change is a function of both the quantity of material in the microwave path and its content, but it is a different function so that both density and percent water can be computed. In effect, attenuation is proportional to the imaginary part of the dielectric constant $\epsilon_2$ of the material and phase change proportional to the real part $\epsilon_1$.

The dielectric constant $\epsilon$ of any material is a complex quantity as expressed by the equation:

$$\epsilon = \epsilon_1 = i\epsilon_2$$

Where i is the square root of minus one. Both 68 $_1$ and $\epsilon_2$ are functions of both density and water content so that if density is constant, either attenuation or phase change could be used to measure percent water, but because the water resonance principally affects $\epsilon_2$ it is more sensitive to water and therefore generally preferred, particularly at low moisture levels. In the same way, at low moisture levels, $\epsilon_1$ is more dependent on density than on water content. Nevertheless, phase change can be preferred in some cases for moisture measurement, particularly when electrical conductivity effects are strong because these do not affect $\epsilon_1$ and so do not interfere with phase change measurement.

The thickness of material through which the microwaves are passed is often arranged to be held constant by the geometry of the sensing system but where this thickness does vary it can readily be measured by a variety of well known means such as by a linear resistive transducer or by a linear variable differential transformer.

The bonding saturation level is only required to be known where moisture measurements are required to be made through this level because it is only under those circumstances that two different moisture sensitivity slopes have to be used and their change over point must be known. The bonding saturation level is almost wholly dependent on the fines content of the material which, in many cases, is contributed by a single component of a mixture and the quantity of that component is known or can readily be measured by a standard technique. For example, in foundry molding sand it is the Bentonite clay which contributes the fines content and controls the bonding saturation level and a standard procedure exists for its determination.

It is also a significant part of this invention that if the measurement of the microwave phase change is not needed to determine the material density because the density is constant or is otherwise known, the phase signal can be used to measure bonding because bound water contributes the same as free water to $\epsilon_1$ but not to $\epsilon_2$, whence the microwave phase change is a function of total water, whereas microwave attenuation is a function only of free water.

The application of these ideas, leading to accurate moisture measurement is perhaps best understood by considering one specific case which will illustrate the method and has proved to be highly successful, namely the measurement of moisture in foundry molding sand. When the dry ingredients of such molding sand are first mixed, they cause only small microwave attenuation, but on coming in contact with hot iron, changes are produced so that when the sand is returned for re-use and its moisture content measured, it is found to attenuate the microwaves quite strongly, even when bone dry. This dry sand attenuation has been found to vary, in some cases considerably, from one batch of sand to another. The dry attenuation is, however, found to be independent of microwave frequency, at least over a two to one frequency range as for example between 10.7 GHz and 5.8 GHz and 2.45 GHz. The difference in the attenuations at the two frequencies is therefore independent of the dry sand attenuation and a function only of the water present. It is a function of the water present per unit volume and to present this as percent water it is necessary to divide by the sand density. Now the purpose for which the sand is used requires that it be highly compactable when prepared for use as molding sand. To achieve this, Bentonite clay is added to the sand which has the property that it swells when brought in contact with water. The density of foundry sand is therefore not constant and density measurement is necessary for accurate moisture determination by microwaves.

The bonding saturation level of the water in foundry sand is certainly dependent on the amount of Bentonite clay which is present in the mix, but so is the performance of the sand in its molding function; it is therefore the practice in all foundries to ensure that this is maintained and fresh Bentonite clay is added to achieve this. Provided the water measurement on return sand is done after the Bentonite clay has been so added as required, the bonding saturation level will be above the level of moisture occurring in the return sand so that measurement of this return sand by microwaves will not be effected by the bonding saturation level.

Thus, means to develop two microwave attenuation signals and one phase signal are necessary for accurate moisture measurement in foundry sand.

SUMMARY OF INVENTION

It is therefore one object of the present invention to provide a microwave measurement apparatus for accurately measuring an unknown property of a test material.

Another object of the invention is to provide an improved microwave moisture measurement apparatus which is capable of accurate measurement of moisture content of a test material in the presence of another variable component which is highly absorbent of microwave energy.

A further object of the invention is to provide such an improved moisture measurement apparatus which employs two microwave signals of different frequencies to compensate for the other variable component in the test material.

An additional object of the invention is to provide such an improved moisture measurement apparatus which is capable of accurate measurement of the percent of moisture content even though the density of the test material varies by determining the phase shift of the received signal produced by a microwave beam transmitted through such test material.

Still another object of the invention is to provide an improved microwave antenna which is capable of efficiently transmitting or receiving two microwave beams of different frequencies without appreciable interference.

A still further object of the invent&on is to provide such an improved microwave moisture measurement apparatus employing such an improved antenna for accurate measurement of the moisture content of test material in an efficient manner with a compact apparatus.

BRIEF DESCRIPTION OF DRAWINGS

Other objects and advantages of the present invention will be apparent from the following detailed description of a preferred embodiment thereof and from the attached drawings of which:

FIG. 3 is a schematic diagram showing the electrical circuit for measurement of the phase shift of a received microwave signal to determine the density of the test material, and to combine it with the attenuation measurements of FIG. 2 in order to determine the percent of moisture content in a second embodiment of the microwave moisture measurement apparatus of the present invention;

DESCRIPTION OF PREFERRED EMBODIMENTS

In order to obtain accurate microwave measurement of moisture it has been found to be necessary, in most test materials to make two attenuation measurements with two different microwave frequencies simultaneously and to measure changes in the phase shift at one of them thereby giving three independent measurement signals which are suitably combined in a data processor such as an analog or digital computer to give the moisture content percentage. These measurements are done on test material 1, such as foundry sand, supported in a testing station 2 surrounded by microwave shields 3 such as by transporting such test material on a conveyor belt 4 through such testing station. Two microwave antennas are provided on opposite sides of the conveyor belt. One of the antennas is a transmitting antenna which transmits a beam of microwaves through the test material to a receiving antenna to test a property of the material, such as its moisture content, by determining the amount of microwave beam attenuation due to microwave energy absorption by such moisture or the other property tested.

Figure 1:
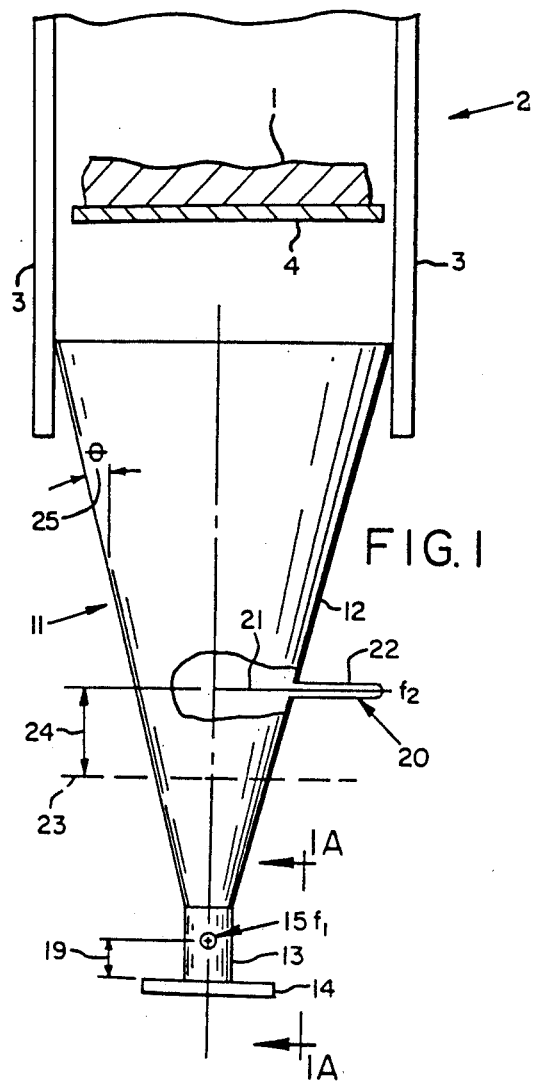
FIG. 1 is a side elevation view of the dual frequency antenna developed for use in an embodiment of the present invention with parts broken away for clarity.
Figure 1A:
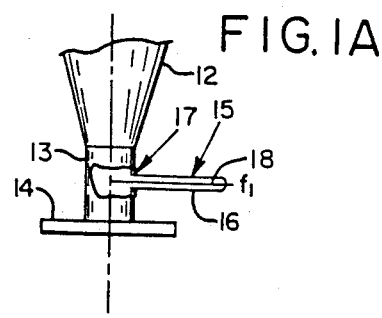
FIG. 1A is a partial elevation view taken along the line 1A—1A of FIG. 1.

In the preferred embodiment of this invention, a single antenna 11 shown in FIG. 1 is used to direct both microwave beams of different frequency through the test material to be measured and a second similar antenna is used to receive both beams. As shown in FIG. 1, the antenna 11 consists of a thin walled conical section 12 and short cylindrical section 13 made of metal or other electrically conductive material and containing a dielectric material. The cylindrical section is closed at one end by a metallic base 14. The higher frequency microwave signal, $f_1$, is fed in through a first coaxial connector 15 with its outer conductor 16 joined electrically to the cylindrical section 13 by soldering at joint 17 and with its center conductor 18 continuing to the center line or longitudinal axis of the antenna, as shown in FIG. 1A. The diameter D of the short cylindrical section 13 is related to the microwave frequency by the requirement that it be greater . than the "cut off" diameter $D_c$ for that frequency given by:

$$D_c = \frac{C}{1.70645 f_1 \sqrt{\epsilon_1}} \qquad \text{Equation 1}$$

Where C is the velocity of light in vacuum, $f_1$ is the frequency of the microwave signal and $\epsilon_1$ is the real part of the dielectric constant of the material filling the cylindrical section. The point at which the coaxial conductor 15 is located along the length of cylindrical section 13 is such that the distance 19 to the closed end of the cylinder is a quarter wavelength, $\lambda_G/4$ where $\lambda_G$ is the wavelength of the microwave of frequency $f_1$ inside the cylinder which is given by the formula:

$$\lambda_G = \frac{C}{\sqrt{\epsilon_1} \sqrt{f_1^2 - f_c^2}} \qquad \text{Equation 2}$$

where $$f_C = \frac{C}{1.70645 D \sqrt{\epsilon_1}}$$

These two equations can be combined to give:

$$\lambda_G = \frac{1.70645 D D_c}{\sqrt{D^2 - D_c^2}} \qquad \text{Equation 3}$$

From which the requirement that $D_c$ be greater than $D$ is apparent.

The lower frequency $f_2$ of the two microwave frequencies is fed into the antenna 11 through a second coaxial connector 20 including an outer conductor 22 joined in the same way as coaxial conductor 15 and with its center conductor 21 similarly extending inward to the center line of the antenna. The point at which the coaxial connector 20 is located along the length of the antenna is required to meet the following conditions. There is a point along the conical section, indicated by the dashed line 23 at which the diameter of the cone is equal to the "cut off" diameter $D_c'$ for the lower frequency $f_2$ given by:

$$D_{c'} = \frac{C}{1.70645 f_2 \sqrt{\epsilon_1}} \qquad \text{Equation 4}$$

This means that microwaves of frequency $f_2$ cannot be transmitted without loss along the small diameter part of the cone. Thus, the cone portion at position 23 acts in effect like an electrical open circuit. The coaxial connector 20 is required to be located a distance 24 outwardly from this open circuit position 23 such that this distance 24 is a half wavelength, $\lambda_G'/2$ where $\lambda_G'$ is the wavelength of the microwave frequency $f_2$ inside the cone. This wavelength $\lambda_G'$ varies along the distance 24 as the cone diameter varies. Integration over this distance gives the value L for the distance 24 from the equation:

$$L^3 = \left(\frac{1.70645 D_{c'}}{2}\right)^2 \left(L + \frac{D_{c'}}{\tan\theta}\right) \qquad \text{Equation 5}$$

Where $\theta$ is the cone angle shown at 25 in FIG. 1.

The coaxial conductors 15 and 20 are spaced 90° apart around the cone circumference, as indicated in FIGS. 1 and 1A so that the plane polarized microwave beams of signal $f_1$ and $f_2$ have their respective planes of polarization at right angles. In this way the receiving antenna, which is identical to the transmitting antenna shown in FIG. 1 can be oriented so that the higher frequency $f_1$ is received only by its coaxial conductor 15 and the lower frequency $f_2$ is received only by its coaxial conductor 20. In this way, the two signals are kept distinct and separate and do not interfere with each other.

The antennas may be filled with air as the dielectric so that $\epsilon_1$ is approximately equal to 1, but in applications where they are transmitting directly into and receiving directly from a test material of higher dielectric constant, they may with advantage be filled with a dielectric of about the same dielectric constant $\epsilon_1$ as that of the test material, thereby improving the antenna's radiating efficiency or enabling a smaller diameter antenna to be used. For example, to measure foundry sand using $f_1 = 10.7$ GHz and $F_2 = 5.8$ GHz, the present inventor has successfully used antennas 5 and ½ inches long with outer diameter of 3 inches and with the cylindrical section being of ⅜ inch diameter using a dielectric material to fill the antennas having a dielectric constant $\epsilon_1$ of 3.8.

As already stated, the same antennas used for attenuation measurements can also provide the sensing elements for measurement of phase change to provide a more compact measurement apparatus. But, whereas, two microwave signals at the two different frequencies are used and combined to provide the attenuation measurement, only one microwave signal is used for phase measurement, and with special microwave components to separate and analyze the signal for phase. The use of a single transmitting antenna and a single receiving antenna for all three measurements is an important feature for accuracy because it ensures that all three measurements are made at the same location at the same instant of time. Furthermore, for foundry sand moisture measurement, there are many foundries where it would be physically impossible to install separate gauges close to each other.

Figure 2:
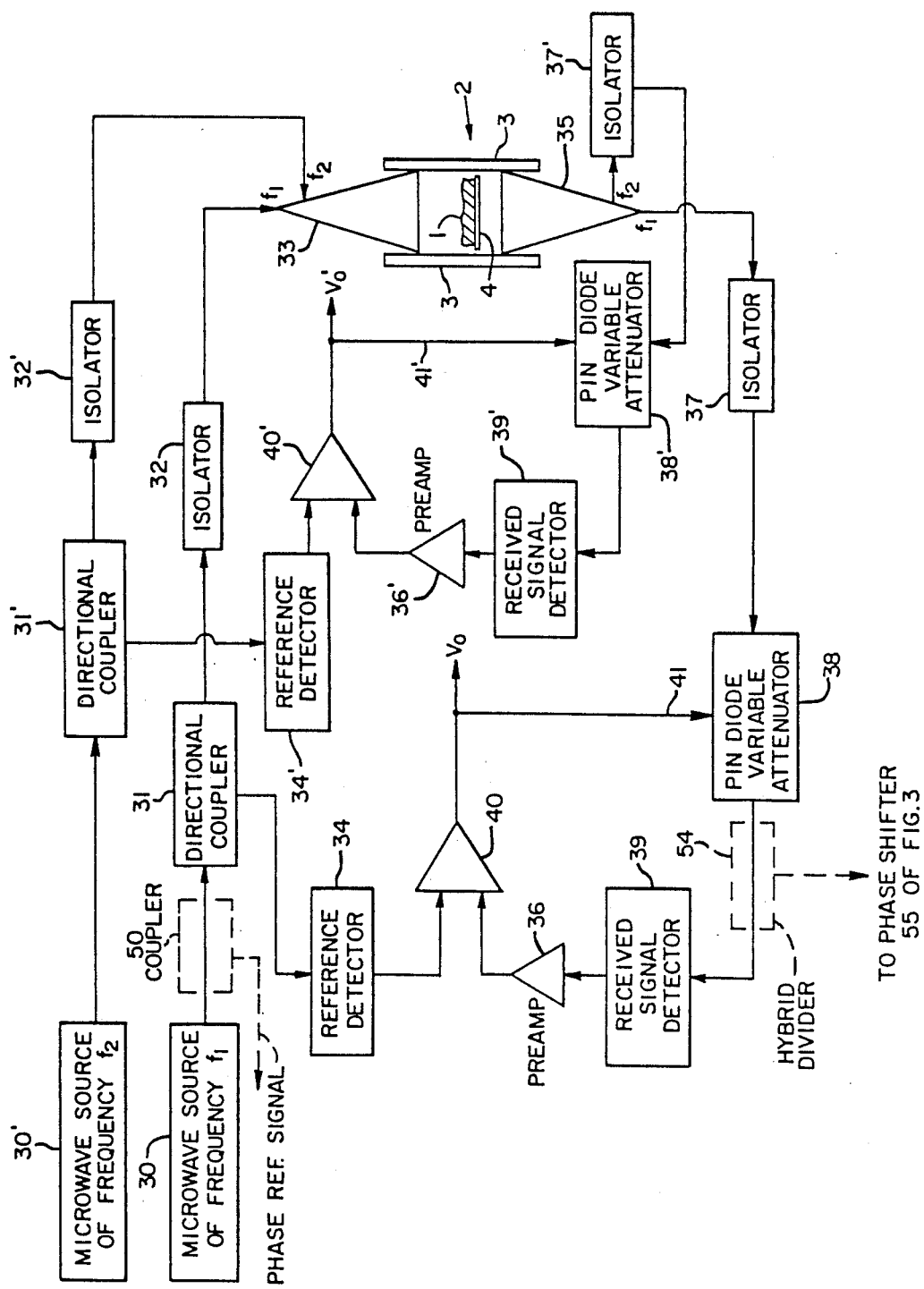
FIG. 2 is a schematic diagram showing the electrical circuit for the measurement of microwave attenuation by moisture in a test material at two different microwave frequencies to determine moisture content in one embodiment of the present invention.

FIG. 2 is a block schematic diagram which shows the microwave devices and other electronic components in the preferred embodiment of the microwave measurement apparatus of the invention, which are used to generate output signals Vo and Vo' proportional to attenuation of the microwave beam by the test material for each of the two frequencies $f_1$ and $f_2$ in accordance with the formulas:

$$a = K_1 W d + K_2 d \qquad 6$$
$$ti\ a' = K_3 W d + K_2 d \qquad 7$$

Where a, a' are the attenuations in decibels for the two frequencies $f_1$ and $f_2$, and where $K_1$, $K_2$, $K_3$ are constants, W is percent water and d is density of the test material. In FIG. 2, a microwave source 30 generates an amplitude modulated microwave signal of a high frequency $f_1$ of, for example 10.7 GHz which passes through the directional coupler 31 and isolator 32 to connector 15 of a transmitting antenna 33 which is like antenna 11 in FIG. 1. The directional coupler 31 feeds a small part, generally between 0.1 percent and 1.0 percent of the signal $f_1$ to a reference detector 34 which produces a reference signal whose amplitude is proportional to the microwave power passed to the transmitting antenna.

The received microwave signal after passing through the moist test material 1 is passed from the connector 15 of a receiving antenna 35 through another isolator 37 to the input of a PIN diode variable attenuator 38 which further attenuates the signal to produce a constant signal level at the input to the signal detector 39 connected to the output of such attenuator. This constance is achieved by comparing the attenuated received signal from the signal detector 39 after it is amplified by preamplifier 36 to a fixed fraction of the reference signal from the reference detector 34 which are applied to the inputs of a high gain differential amplifier 40 to produce an attenuated output signal, Vo, proportional to the attenuation of the test material as given in Equation 6. The output signal, Vo, of differential amplifier 40 is also applied at control terminal 41 of the attenuator 38, making a closed loop, negative feedback arrangement. As a result of such negative feedback, any difference between the two compared signals at the inputs of amplifier 40 causes a change in attenuation of the received signal by the PIN diode attenuator as needed to bring the microwave signal level at the input of signal detector 39 to the desired constant value. The same circuit operation occurs when the second microwave signal of low frequency $f_2$ of, for example, 5.86 GHz is transmitted from source 30' through coupler 31' and isolator 32' to the coaxial connector 20 of transmission antenna 33. Therefore, such operation of the second attenuation circuit including isolator 37', variable attenuator 38', signal detector 39', preamplifier 3', reference detector 34' and differential amplifier 40' to produce the second attenuated output signal Vo' will not be described.

Clearly, if there is an increase of attenuation by the moist test material 1 there will be an equal decrease of attenuation by the PIN diode attenuators 38 and 38'. Since the attenuation by the PIN diode attenuator is a direct function of the output signal Vo and Vo' fed to its control input 41 and 41', these output signals provide a direct measure of the attenuations "a" in the moist material at frequencies $f_2$ and f, respectively. Thus, the difference between attenuation a and attenuation a' obtained by subtracting Vo' from Vo is proportional to the amount of moisture in the test material.

For phase measurement using microwave signal $f_1$ to determine the density of the test material, all the components of the corresponding circuit of FIG. 2 are used as described above for attenuation measurement except only that an additional directional coupler 50 is added between the microwave source 30 and directional coupler 31 to provide a phase reference signal and a hybrid divider 54 is added between the PIN diode attenuator 38 and the signal detector 39. These two added components are fixed passive devices so that their addition leaves the operation of the attenuation loop effectively unchanged.

FIG. 3 is a schematic block diagram of the phase measuring circuit used in one embodiment of the invention. Microwave source 30 transmits microwave signal $f_1$ through the added directional coupler 50 which feeds a small fraction (between 0.1 percent and 1.0 percent) of the signal through a level set attenuator 51 and a fixed attenuator 52 to one input of a hybrid combiner 53 to provide a phase reference signal to this combiner. On the receiving side, the output of PIN diode variable attenuator 38 is connected to the input of added hybrid divider 54 which feeds half the received signal to the attenuation loop 39, 36, 40, 41 of FIG. 2 and the other half of such received signal through a voltage variable phase shifter 55 whose output is connected to the other input of the combiner 53.

The voltage variable phase shifter 55 is arranged to be swept periodically through a full 360° phase change by the ramp shaped voltage applied to control terminal 71 by a ramp generator 56. As a result, the phase of the phase shifted received signal applied by shifter 55 to the second input to the hybrid combiner is swept periodically through 360°.

Figure 4:
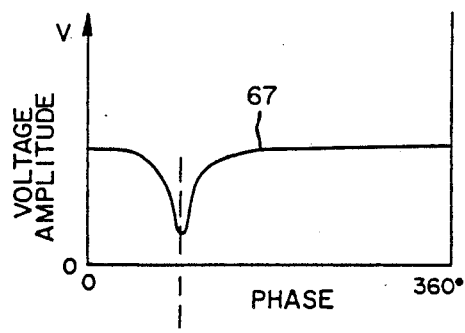
FIG. 4 shows the electrical signal produced at test point TP 1 in FIG. 3, plotted through one 360° phase sweep of the phase shifter of FIG. 3.

The hybrid combiner 53 combines the two input signals so that its combined output signal is the vector sum of such two input signals. If, therefore, the two input signals are of equal amplitude there will be one point in the 360° sweep where the two signals are 180° out of phase with each other and the hybrid combiner output will dip to a minimum amplitude. The operation of the attenuator loop of attenuator 38 ensures that the signal level at the output of the attenuator remains constant and is a constant fraction of the phase reference output signal of the directional coupler 50. The level set attenuator 51 is therefore adjusted to make the amplitudes of the two input signals of the hybrid combiner 53 equal. The output from the hybrid combiner 53 passes through the phase signal detector 57 which gives a detected output signal whose amplitude is proportional to the amplitude of the combined output signal of the hybrid combiner and which therefore goes through a sharp minimum at one point in each 360° sweep of the ramp generator. It should be noted that each sweep can be less than 360° if it includes the sharp minimum. This detected signal is amplified by amplifier 58, rectified by a full wave rectifier 59 and filtered by filter 60 to give a phase shift indication signal 67 at test point No. 1 as shown graphically in FIG. 4. The low pass filter 60 between the rectifier 59 and TP1 serves to clean up this signal by removing noise and unwanted components from the signal.

Figure 5:
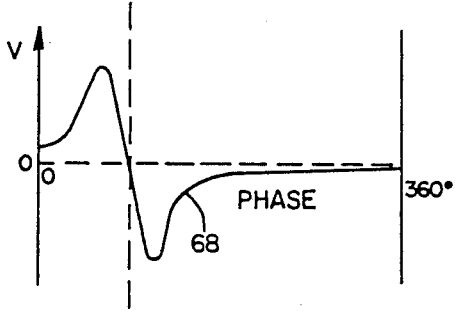
FIG. 5 shows the electrical signal produced at TP 2 in FIG. 3, plotted through the same 360° phase sweep of FIG. 4.
Figure 6:
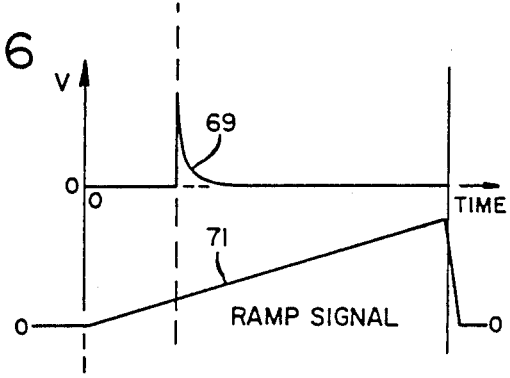
FIG. 6 shows the electrical pulse produced at TP 3 in FIG. 3, and the ramp voltage produced by the ramp generator of FIG. 3.
Figure 7:
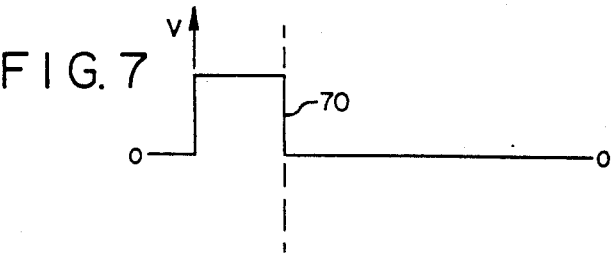
FIG. 7 shows the electrical signal produced at TP 4 in FIG. 3 shown on the same time scale as the signals of FIG. 6.

A differentiation circuit 61 converts the signal from TP1 to the differentiated phase shift indication signal 68 of the waveform indicated in FIG. 5 at TP2 in which there is a sharp transition through zero. The comparator 62 and capacitor 63 serves to convert this signal into a sharp positive spike pulse 69 at TP3 corresponding to the zero crossing of signal 68 and applies such spike pulse to one input of the latch 64 and as shown in FIG. 6. The other input to the latch 64 is a second sharp spike pulse produced by the voltage transition at the end of the previous ramp signal (not shown) and corresponding to the start of the ramp voltage signal 71 of FIG. 6 which comes from the ramp generator circuit 56 so that a positive rectangular latch output pulse 70 produced at TP4 is initiated at the start of each ramp and is terminated by spike pulse 69 at the phase signal minimum point as shown in FIG. 7. This is repeated for each repetitive 360° sweep of the ramp generator and so produces a pulse train with pulses 70 of constant amplitudes and variable pulse widths with their pulse width proportional to the phase shift of the minimum point in signal 67 corresponding to the output from the hybrid combiner 53. The integrator 65 which integrates this pulse train therefore gives a phase shift output signal, Vp, whose voltage level is proportional to this phase shift.

The phase shift signal Vp is approximately proportional to the density of the test material in the following equation for the moisture range of 0 to 4 percent moisture which applies to foundry molding sand.

$$\log \epsilon_m = C_1 W d + C_2 d \qquad 8$$

where $\epsilon_m$ is the dielectric constant of the mixture of air, water and sand in the test material, $C_1$ and $C_2$ are constants related to the dielectric constants of water and said, W is the percent of water and d is the density of the test material.

The zero level of this phase shift output signal Vp corresponds to the phase of the received signal which would produce a hybrid combiner output signal minimum at the start of each ramp. This can be adjusted to a desired minimum corresponding, for example, to some minimum density at zero percent water by adjustment of a preset line stretcher 70 or other presetable phase shifter provided at the input of attenuator 38, as shown in FIG. 3. The phase shift output signal Vp of integrator 65 and the attenuation output signals Vo and Vo' of the differential amplifiers 40 and 40' of FIG. 2 are applied to the inputs of a data processor 66, such as an analog or digital computer, which combines such signals in accordance with Equations 6, 7 and 8 to produce a percent moisture content signal at the output of such data processor which indicates the amount of moisture in the test material 1.

It will be obvious to those having ordinary skill in the art that many changes may be made in the above described preferred embodiment of the present invention. Therefore, the scope of the present invention is to be determined by the following claims.

I claim:

1. Microwave antenna apparatus for measuring the moisture content of material, comprising:
   a first antenna portion of conical shape;
   a second antenna portion of circular cylindrical shape having one end closed and joined at its open end to the small end of said first antenna portion and coaxial therewith, said second antenna portion being of substantially the same diameter as said small end of said first antenna portion;
   a first microwave signal connection means connected to the side of said first antenna portion for transmitting a first microwave signal;
   a second microwave signal connection means connected to the side of said second antenna portion for transmitting a second microwave signal of different frequency than said first microwave signal;
   said first and second connection means being spaced apart by a longitudinal distance along the axis of the antenna and by a circumferential displacement angle about the axis of the antenna; and
   said second connection means being spaced from a closed end of the second antenna portion by an old multiple of a quarter wavelength of the second microwave signal and said first connection means being spaced from a point on the first antenna portion where the diameter of its cone is equal to the microwave cut-off diameter for the frequency of the first microwave signal by a distance which is a multiple by a half wavelength of the first microwave signal.

2. Antenna apparatus in accordance with claim 1 in which the displacement angle is approximately 90 degrees.

3. Microwave antenna apparatus for measuring a property of a material, comprising:
   a first antenna portion of tapered shape and circular cross-section;
   a second antenna portion of circular cylindrical shape having one end closed and joined at its open end to the small end of said first antenna portion and coaxial therewith, said second antenna portion being of substantially the same diameter as said small end of said first antenna portion so that there is a gradual transition between said first and second antenna portions;
   a first microwave signal connection means including a first coaxial conductor connected to the side of said first antenna portion for coupling a first microwave signal;
   a second microwave signal connection means including a second coaxial conductor connected to the side of said second antenna portion for coupling a second microwave signal of different frequency than said first microwave signal; and
   said second connection means being spaced from a closed end of the second antenna portion by an odd multiple of a quarter wavelength of the second microwave signal and said first connection means being spaced from a point on the first antenna portion where the diameter of its cone is equal to the microwave cut-off diameter for the frequency of the first microwave signal by a distance which is a multiple of a half wavelength of the first microwave signal.

4. Apparatus in accordance with claim 3 in which said first and second connection means are coaxial connectors spaced apart by a longitudinal distance along the axis of the antenna to provide an open microwave path between said first and second connection means which is free of electrical conductors.

5. Apparatus in accordance with claim 4 in which said first and second connection means are spaced apart by a circumferential displacement angle of approximately 90° about the axis of the antenna.

6. Apparatus in accordance with claim 3 in which the tapered shape is conical.

* * * * *